(12) United States Patent
Janevski et al.

(10) Patent No.: US 11,348,662 B2
(45) Date of Patent: May 31, 2022

(54) BIOMARKERS BASED ON SETS OF MOLECULAR SIGNATURES

(75) Inventors: Angel Janevski, New York, NY (US); Vinay Varadan, New York, NY (US); Nilanjana Banerjee, Armonk, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/321,723

(22) PCT Filed: May 18, 2010

(86) PCT No.: PCT/IB2010/052208
§ 371 (c)(1),
(2), (4) Date: Jan. 30, 2012

(87) PCT Pub. No.: WO2010/134023
PCT Pub. Date: Nov. 25, 2010

(65) Prior Publication Data
US 2012/0265446 A1  Oct. 18, 2012

Related U.S. Application Data

(60) Provisional application No. 61/179,847, filed on May 20, 2009.

(51) Int. Cl.
*G16B 40/00* (2019.01)
*G16B 25/10* (2019.01)
*G16B 25/00* (2019.01)

(52) U.S. Cl.
CPC ............ *G16B 40/00* (2019.02); *G16B 25/10* (2019.02); *G16B 25/00* (2019.02)

(58) Field of Classification Search
None
See application file for complete search history.

(56) References Cited

U.S. PATENT DOCUMENTS

| 2007/0192061 A1 | 8/2007 | Kanevsky et al. |
| 2008/0097939 A1 | 4/2008 | Guyon et al. |
| 2008/0305965 A1 | 12/2008 | Moorhouse et al. |

FOREIGN PATENT DOCUMENTS

| CN | 1604112 A2 | 4/2005 |
| JP | 2008536488 A | 9/2008 |
| JP | 2009509502 A | 3/2009 |
| WO | 2008027912 A2 | 3/2008 |

OTHER PUBLICATIONS

Non-patent literature Liu Hui, "Classification prediction of protein sequence data", (Oct. 15, 2007), No. 4, p. 1-99.

*Primary Examiner* — Eric S DeJong
(74) *Attorney, Agent, or Firm* — Micah-Shalom Kesselman

(57) ABSTRACT

A method (10) for forming novel signatures of biological data is provided. The method comprises ranking features based on a trend value, which is created based on multiple signatures identified by a pattern discovery method. Furthermore, a device (30) and a computer program product (40), performing the steps according to the method (10) is provided. Uses of the method, for statistically analyzing clinical data, designing assays based on multiple molecular signatures and interpreting assays based on multiple molecular signatures are also provided.

7 Claims, 3 Drawing Sheets

BIOMARKERS BASED ON SETS OF MOLECULAR SIGNATURES

FIELD OF THE INVENTION

This invention pertains in general to the field of bioinformatics. More particularly the invention relates to a method for forming novel signatures of biological data based on ranking multiple signatures of biological data. The invention also relates to a device for comparing multiple molecular signatures, a device to forming novel signatures, a computer program product and uses of said method and device.

BACKGROUND OF THE INVENTION

It is known that high-throughput molecular profiling of biological samples has resulted in signatures used to stratify the samples into particular categories. Such groups may be diagnosis of condition (normal vs. disease), disease course (aggressive vs. non-aggressive) or therapy selection (drug response). Examples of signatures are molecular signatures.

Signatures, such as molecular signatures, are typically discovered and validated through clinical studies, but it has been established that there is a great variability in the contents of such signatures when they are answering the same clinical question. This is primarily due to the nature of the data available for analysis—high-throughput measurements provide features in the tens or hundreds of thousands, whereas the number of measurements points (samples) is in the hundreds. This is also referred to as the curse of dimensionality given the several-orders-of-magnitude disparity between the number of features and the number of samples. Furthermore, even within the context of the same clinical study and the same discovery method, it is often the case that repeating the exact same procedure with variability in the choice of parameters, or different randomization, will lead to similar but nonetheless different signatures.

The fast development within the art has given rise to many signatures that stratify patients into particular categories. This data is often incoherent and diverse, since no particular standard exists. The complex nature of biological systems, and the way these are studied, also makes it difficult to compare sets of genomic identities of different origin.

Hence, an improved method for analysis of biological data would be advantageous and in particular a method allowing for increased flexibility, cost-effectiveness, speed and/or analytical precision would be advantageous.

SUMMARY OF THE INVENTION

Accordingly, the present invention seeks to mitigate, alleviate or eliminate one or more of the above-identified deficiencies in the art and disadvantages singly or in any combination. This object is achieved by providing a method, a device, a computer program product and a use to group multiple signatures of biological data, according to the appended independent patent claims.

A general solution according to the invention is to enable measurement of multiple signatures of the same predictive value.

According to a first aspect of the invention, a method is provided, for forming novel signatures of biological data comprising a number of features ($F=\{F_1, F_2, \ldots, F_n\}$) based on analyzing a set of multiple signatures of biological data. Said method comprises the step of obtaining a set of multiple signatures of biological data by running a feature subset selection algorithm on the biological data N times. For each run ($r_i$) of a number of runs ($\{r_1, r_2, \ldots, r_N\}$), the method also comprises the steps of forming a first matrix ($M_i$) of size (F×F), wherein each matrix element (i,j) of the first matrix ($M_i$) quantifies each corresponding feature-pair ($F_iF_j$) based on their co-occurrence in the analyzed signatures in run $r_i$; and forming a second matrix (T) of size (F×N), wherein each element ($T_{(i,j)}$) of the second matrix (T) is assigned the sum of the corresponding row ($F_i$) of the corresponding first matrix ($M_i$). Furthermore, the method comprises forming a vector (C) of size (F) wherein each element ($C_{Fi}$) of said vector is assigned the average of the corresponding row ($T_i$) for all columns (1 to N) of the second matrix (T). The method further comprises sorting each value of vector (C) in descending order, resulting in ranking each feature ($F_i$) represented by each element of the vector (C) in descending order. The method also comprises forming a novel set of signatures based on the ranked features by combining at least two features of signatures with similar ranking.

According to a second aspect of the invention, a device is provided, comprising units configured to perform the steps according to the first aspect of the invention, when said units are operatively connected to each other.

According to a third aspect of the invention, a computer program product comprising a computer program for processing by a computer is provided. The computer program comprises a code segment for performing the method according to the first aspect of the invention.

According to a fourth aspect of the invention, use of the method according to the first aspect or the device according to the second aspect, for statistically analyzing clinical data is provided.

According to a fifth aspect of the invention, use of the method according to the first aspect or the device according to the second aspect, for designing assays based on multiple molecular signatures is provided.

According to a sixth aspect of the invention, use of the method according to the first aspect or the device according to the second aspect, for interpreting assays based on multiple molecular signatures is provided.

Embodiments of the invention are defined in the dependent claims.

The present invention has an advantage over the prior art in that it allows a more comprehensive output from the signature discovery process. Instead of a rigid single-signature output, a broader description trend is captured which enables multiple clinical views of a single set of measurements. This description may be utilized in a variety of ways. In clinical research, multiple signatures allows for better assessment of the biology underlying the clinical question being investigated. This can be used, for example, to search for multiple drug targets and assess disease mechanisms. Furthermore, in designing diagnostic assays, the invention allows for multiple signatures of the same predictive value to co-exist. This can help, for example, circumvent problems in assay design by enabling selection of most optimal set of genomic features. The clinician is able to apply different views on the patient data, thus taking advantage of many combinations of genomic features and selecting the most optimal ones to best describe the biological state of the physiological sample and clinical state of the patient.

Instead of a rigid single-signature output, a broader description trend is captured which enables multiple clinical views of a single set of measurements. This description can be utilized in a variety of ways. In clinical research, instantiating multiple signatures allow for better assessment of the biology underlying the clinical question being investigated.

A further advantage is that the invention allows application of different views on patient data, thus taking advantage of many combinations of genomic features and selecting the most optimal ones to best draw conclusions from genetic information.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Figure 1:
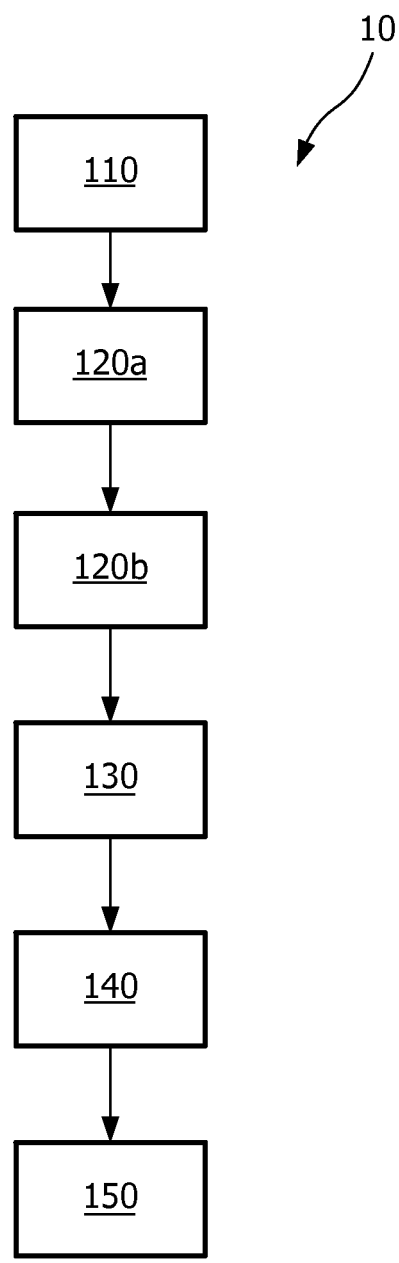
FIG. 1 is a flowchart of a method according to an embodiment.

In an embodiment according to FIG. 1, a method 10 is provided for forming novel signatures of biological data comprising a number of features ($F=\{F_1, F_2, \ldots, F_n\}$) based on analyzing a set of multiple signatures of biological data. In a step 110, said method comprises obtaining a set of multiple signatures of biological data by running a feature subset selection algorithm on the biological data N times. For each run ($r_i$) of a number of runs ($\{r_1, r_2, \ldots, r_N\}$), the method 10 comprises a step 120a for forming a first matrix ($M_i$) of size (F×F), wherein each matrix element (i,j) of the first matrix ($M_i$) quantifies each corresponding feature-pair ($F_i F_j$) based on their co-occurrence in the analyzed signatures in run $r_i$; and a step 120b for forming a second matrix (T) of size (F×N), wherein each element ($T_{(i,j)}$) of the second matrix (T) is assigned the sum of the corresponding row ($F_i$) of the corresponding first matrix ($M_i$). In a step 130, the method 10 further comprises forming a vector (C, e.g. $C=C_{F1}, C_{F2}, \ldots, C_{Fn}$) of size (F) wherein each element ($C_{Fi}$) of said vector is assigned the average of the corresponding row ($T_i$) for all columns (1 to N) of the second matrix (T). The method comprises a step 140 for sorting each value of vector (C) in descending order, resulting in ranking each feature ($F_i$) represented by each element of the vector (C) in descending order. Furthermore, the method 10 comprises a step 150 for forming a novel set of signatures based on the ranked features by combining at least two features of signatures with similar ranking.

Signatures are described through characterization, such as ranking of the measured molecular features and a trend, such as feature co-occurrence may be created, that helps determine which features may be combined and in what order. In addition, families of molecular signatures may be constructed (instantiated). These may be used to design diagnostic assays or explore molecular measurements by varying sets of genomic features. Additional properties for each run may be preserved and taken into account, for example the average feature subset size, average performance (e.g. in classification of samples).

In an embodiment, said signatures could be molecular signatures, such as any signatures chosen from the group comprising nucleotide sequence, genetic variation, methylation status or genetic expression. However, any signature may be utilized.

In an embodiment, said feature subset selection may comprise filtering techniques, forward feature selection techniques, genetic algorithms etc, which are well known in the field. However, any feature subset selection may be utilized.

TABLE 1

An overview of the input to a method according to an embodiment.

| Component | Description |
|---|---|
| M = Genetic Algorithm wrapper of a Support Vector Machine classifier | Given a set of samples each characterized by a vector of measurements, the output is sets of feature subsets that best enable accurate classification of the samples into given categories. |
| S = set of feature subset sets | In each run, preserve the set of feature subsets at the end of the run. |
| T = pairwise co-occurrence of features | In each run, FxF array is first set up and every time features i and j occur together in a feature subset, the counter at (i, j) and (j, i) is increased by 1. Finally, each row is summed up and this is the trend vector for the run. The total trend T is an FxN matrix of trends of individual runs. |
| C - overall characterization. | A vector of F values which average the rows in the trend T. When sorted by the values, features are ranked in descending order. |

In a more specific embodiment based on the programming language "R", the following steps are performed, using the input from table 1:

Input:
C,
T (used to find correlated and anti-correlated features),
number.of.levels,
features.added.per.level
comment: level 1 (add top ranked features)
Subsets = ∅
Subsets = {C[1]}
Add.In.Next.Level = ∅
Repeat (features.added.per.level−1) times (counting in idx from 2 to features.added.per.level)
For all sets AS in Subsets that contain anti-correlated features with C[idx]
Subsets ={Subsets, replace(AS, C[idx], anti-correlated feature)}
For all other sets
For all subsets S in Subsets
S = {S, C[idx]}
Add.In.Next.Level = {Add.In.Next.Level, most.correlated.feature(C[idx])
comment: level 1 (add top ranked features)
Repeat number.of.levels−1 times
Add.In.Previous.Level = Add.In.Next.Level
Add.In.Next.Level = ∅
Repeat features.added.per.level times (counting in idx)
For all sets AS in Subsets that contain anti-correlated features with Add.In.Previous.Level [idx]
Subsets = {Subsets, replace(AS, Add.In.Previous.Level [idx], anti-correlated feature)}

-continued

```
For all other sets
For all subsets S in Subsets
S = {S, Add.In.Previous.Level [idx]}
Add.In.Next.Level = {Add.In.Next.Level,
    most.correlated.feature(Add.In.Previous.Level [idx])}
```

According to the above pseudocode, the most correlated and most ant-correlated features are obtained in a similar way, based on the "neighborhood" of features based on T. One way to do this is to look for the top N correlated (or anti-correlated) features and then using C, to pick the top-ranked one from the N features. Using this approach less-relevant features that are (anti-)correlated but only in a small number of cases may be avoided.

Figure 2:
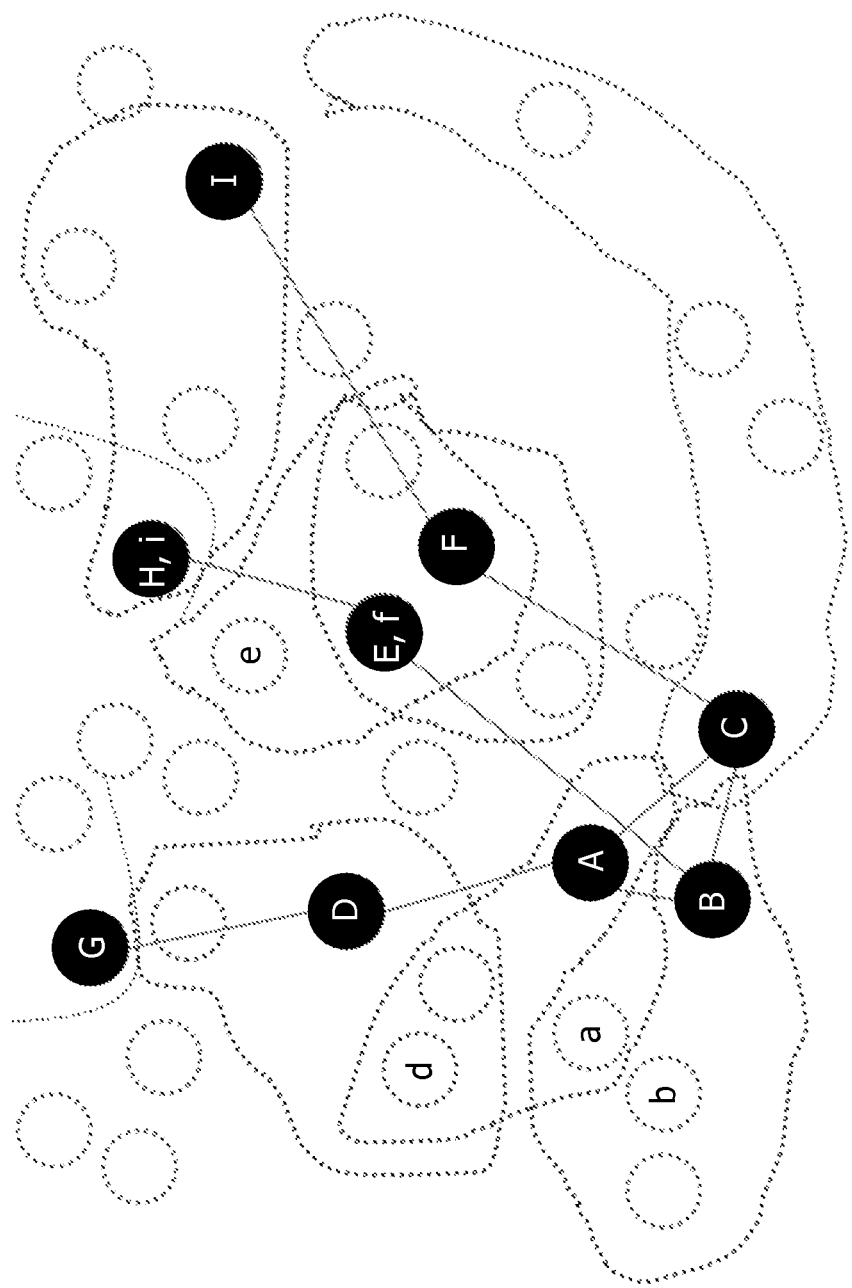
FIG. 2 is a graphic representation of feature subset generation according to an embodiment.

According to FIG. 2, feature subset generation is further described.

Notes in capital letters indicate features as they are added to the subsets. For each of these, a small-case node is marked that indicates the anti-correlated genes. Of these, only the cases when a single node has both a capital and small letter are interesting. Dotted regions indicate the features that are considered for top anti-correlated features. Features considered for addition based on high correlation are not shown for simplification of visualization.

In level 1, Subsets={{A}}, then, B and C are added (features.added.per.level=3) and with those D, E, and F are marked for addition in the next level. A neighborhood of 4 (anti-)correlated features is considered. After level 1, S={{{A,B,C}}, since there were no anti-correlation conflicts so far.

In level 2, D is added to subsets and G is considered to be added in the next level, Subsets={{A,B,C,D}}. Next, E is added to subsets and H is considered to be added in the next level, Subsets={{A,B,C,D,E}}. F is added to subsets and I is considered to be added in the next level, but E and F are not to be used together, so Subsets={{A,B,C,D,E},{A,B,C,D,F}}

In level 3, G is added to subsets, Subsets={{A,B,C,D,E,G},{A,B,C,D,F,G}}, H is added to subsets, Subsets={{A,B,C,D,E,G,H},{A,B,C,D,F,G,H}}, I is added to subsets, with I and H not to be used together, so Subsets={A,B,C,D,E,G,H}, {A,B,C,D,F,G,H}, {A,B,C,D,E,G,I}, {A,B,C,D,F,G,I}}.

Thus, the above example shows how it is possible to use the pair-wise trend values such as correlations and anti-correlations between features to derive novel signatures.

In an embodiment, where N is 4, i.e. the feature subset selection algorithm, which may be any feature subset algorithm known within the art, is run 4 times to obtain 110 a set of multiple signatures of biological data. Based on these signatures, a first matrix ($M_i$) is formed 120a, as shown in Table 2.

TABLE 2

A first matrix $M_i$ according to an embodiment, i = 4.

|    | A   | B   | C   | D   | E   |
|----|-----|-----|-----|-----|-----|
| M1 |     |     |     |     |     |
| A  |     | 450 | 100 | 350 | 30  |
| B  | 450 |     | 30  | 150 | 35  |
| C  | 100 | 30  |     | 50  | 100 |
| D  | 350 | 150 | 50  |     | 30  |
| E  | 30  | 35  | 100 | 30  |     |
| M2 |     |     |     |     |     |
| A  |     | 100 | 400 | 60  | 300 |
| B  | 100 |     | 100 | 60  | 35  |
| C  | 400 | 100 |     | 50  | 50  |
| D  | 60  | 60  | 50  |     | 30  |
| E  | 300 | 35  | 50  | 30  |     |
| M3 |     |     |     |     |     |
| A  |     | 420 | 100 | 300 | 70  |
| B  | 420 |     | 30  | 450 | 35  |
| C  | 100 | 30  |     | 50  | 100 |
| D  | 300 | 450 | 50  |     | 30  |
| E  | 70  | 35  | 100 | 30  |     |
| M4 |     |     |     |     |     |
| A  |     | 100 | 500 | 50  | 300 |
| B  | 100 |     | 100 | 40  | 35  |
| C  | 500 | 100 |     | 50  | 40  |
| D  | 50  | 40  | 50  |     | 30  |
| E  | 300 | 35  | 40  | 30  |     |

Next, a second matrix (T) is formed 120b according to Table 3.

TABLE 3

The second matrix T according to an embodiment.

| T | r1  | r2  | r3  | r4  |
|---|-----|-----|-----|-----|
| A | 930 | 860 | 890 | 950 |
| B | 665 | 295 | 935 | 275 |
| C | 280 | 600 | 280 | 690 |
| D | 580 | 200 | 830 | 170 |
| E | 195 | 415 | 235 | 405 |

Based on the second matrix (T), the C vector is formed 130 by assigning the average of the corresponding row ($T_i$) for all columns (1 to N) of the second matrix (T). The C vector is also sorted 140 in descending order according to Table 4.

TABLE 4

The C vector according to an embodiment.

| C | rank   |
|---|--------|
| A | 907.50 |
| B | 542.50 |
| C | 462.50 |
| D | 445.00 |
| E | 312.50 |

Next, a novel set of signatures may be formed 150 based on the ranked features. In this embodiment, A is the top one. Then, to decide what to add, the features with similar ranking, i e correlated features, but also the non-related, i.e. anti-correlated features, are needed. This may be made by computing a correlation for feature pairs based on the T matrix. The result shown in Table 5.

TABLE 5

Correlated and anti-correlated features in an embodiment.
Numbers within parentheses are negative.

|   | A | B | C | D | E |
|---|---|---|---|---|---|
| A | 1.0000 | (0.0971) | 0.0860 | (0.0977) | (0.1616) |
| B | (0.0971) | 1.0000 | (0.9278) | 0.9995 | (0.8763) |
| C | 0.0860 | (0.9278) | 1.0000 | (0.9386) | 0.9681 |
| D | (0.0977) | 0.9995 | (0.9386) | 1.0000 | (0.8882) |
| E | (0.1616) | (0.8763) | 0.9681 | (0.8882) | 1.0000 |

Starting from feature {A}, the next top-ranked feature is added, giving {A, B}. The next top-ranked feature (C), is not added due to the high anti-correlation between B and C. Instead, two sets are generated, {{A, B}, {A, C}}. In the following, it is similarly not possible to keep D and E together as they are also highly anti-correlated. Thus, the novel set of signatures formed 150 is {{A, B, D}, {A, C, E}} in this embodiment.

Additional properties for each run of the feature subset algorithm, well known in the art, may be preserved and taken into account. In an embodiment, the average feature subset size, average performance in classification of samples etc. may be considered. For example, statistics, such as the average number of features, may be employed in the feature subsets. One subset could have 20 features, while another may have 35 features, etc. Furthermore, the performance of each feature subset in terms of its predictive power of the outcome may be different. For example, one of the subsets may have a prediction accuracy of 98% whereas another one has an accuracy of 95%, etc. Thus, while computing the characterization C of the features, one could weigh the contribution of each subset in terms of its performance. Therefore, if a pair of features seem to occur together in signatures with lower predictive performance, this may be regulated by penalize those pair-wise co-occurrence score by some amount inversely proportional to the average prediction accuracy of the signatures. For example, instead of adding 1 for co-occurrence, 0.5 may be added for subsets that perform worse.

In a clinical embodiment, a clinician may apply different views on the patient data, thus taking advantage of many combinations of genomic features and selecting the most optimal ones to best describe the biological state of the physiological sample and clinical state of the patient. For example, if an assay measures 100 genomic futures from a patient sample, instead of having "one shot" at a set of measurements, a diagnostic test could consist of multiple assessments based on a single study. So, instead of a single test, a committee of signatures may be used that collectively determine the outcome of the test. For example, if based on a clinical study, a trend based on 5 genomic features A, B, C, D, and E may be captured by the 3 combinations A, B, C; A, C, D; A, C, E; then a noisy measurement of feature B would skew the output from the A, B, C. However, the remaining two novel signatures will still accurately catch the signal in the sample.

Figure 3:
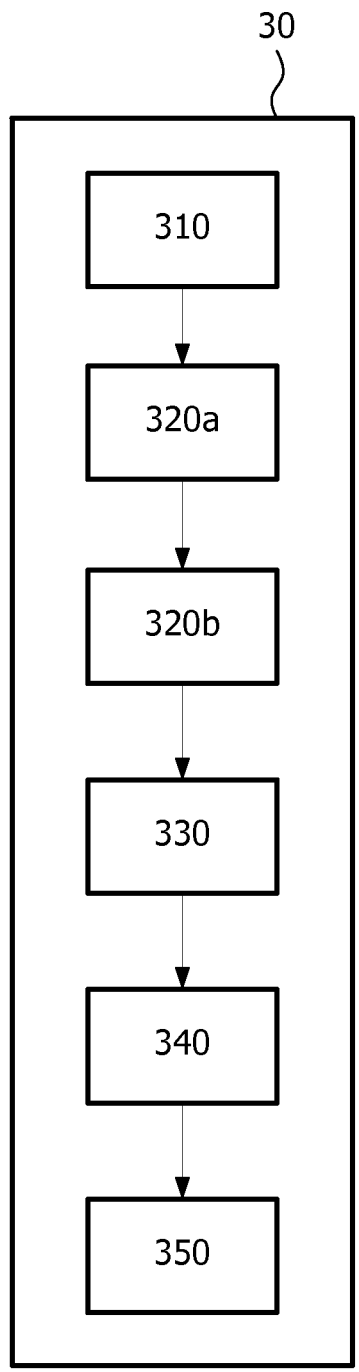
FIG. 3 is a schematic representation of a device according to an embodiment.

In another embodiment of the invention according to FIG. 3, a device 30 for forming novel signatures of biological data is provided. Said device 30 comprises a first unit 310 configured to configured to obtain a set of multiple signatures of biological data by running a feature subset selection algorithm on the biological data N times.

The device 30 also comprises a second unit 320 configured to, for each run ($r_i$), of a number of runs ({$r_1$, $r_2$, ..., $r_N$}) form 320a a first matrix ($M_i$) of size (F×F), wherein each matrix element (i,j) of the first matrix ($M_i$) quantifies each corresponding feature-pair ($F_iF_j$) based on their co-occurrence in the analyzed signatures in run $r_i$; and form 320b a second matrix (T) of size (F×N), wherein each element ($T_{(i,j)}$) of the second matrix (T) is assigned the sum of the corresponding row ($F_i$) of the corresponding first matrix ($M_i$).

The device 30 further comprises a third unit 330 configured to form a vector (C, e.g. C=$C_{F1}$, $C_{F2}$, ... $C_{Fn}$) of size (F) wherein each element ($C_{Fi}$) of said vector is assigned the average of the corresponding row ($T_i$) for all columns (1 to N) of the second matrix (T).

The device 30 comprises a fourth unit 340 configured to sort each value of vector (C) in descending order, resulting in ranking each feature ($F_i$) represented by each element of the vector (C) in descending order.

The device 30 further comprises a fifth unit 350 configured to form a novel set of signatures based on the ranked features by combining at least two features of signatures with similar ranking.

The units 310, 320, 330, 340, 350 are operatively connected to each other. The units 310, 320, 330, 340, 350 may be embodied as separate physical entities, connected together. However, the units 310, 320, 330, 340, 350 may also be embodied in a singular physical entity. Any combination of the units 310, 320, 330, 340, 350 may be embodied in different separate or unified physical entities. Said entities may further be combined in any setup, forming a connection between the physical entities.

The units 310, 320, 330, 340, 350 may be any units normally used for performing the involved tasks, e.g. a hardware, such as a processor with a memory.

In an embodiment the device 30 or the system 100 is comprised in a medical workstation or medical system, such as a Computed Tomography (CT) system, Magnetic Resonance Imaging (MRI) System or Ultrasound Imaging (US) system.

Figure 4:
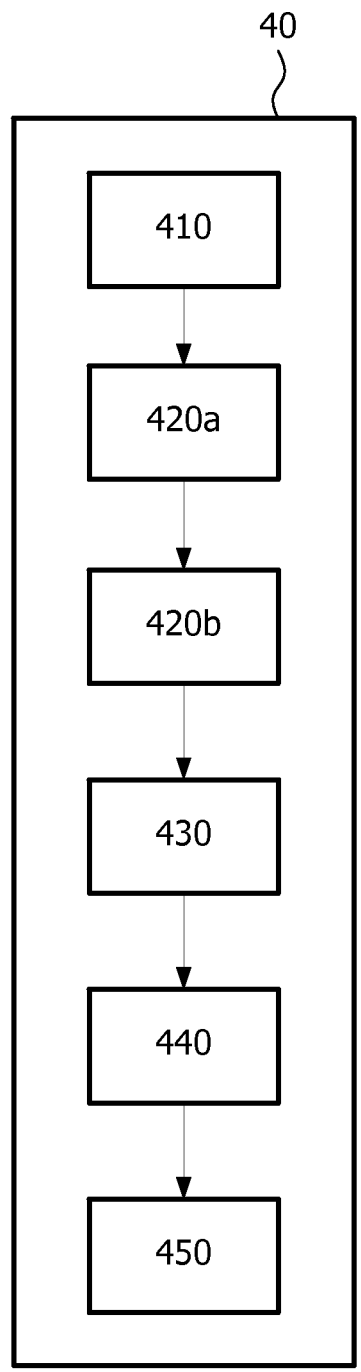
FIG. 4 is a schematic representation of a computer program product according to an embodiment.

In an embodiment according to FIG. 4, a computer program product comprises computer program 40 for processing by a computer. The computer program 40 comprises a first code segment 410 for obtaining a set of multiple signatures of biological data by running a feature subset selection algorithm on the biological data N times, and for each run ($r_i$) of a number of runs ({$r_1$, $r_2$, ..., $r_N$}). The computer program 40 also comprises a second code segment 420 for, for each run ($r_i$) of a number of runs ({$r_1$, $r_2$, ..., $r_N$}) forming 420a a first matrix ($M_i$) of size (F×F), wherein each matrix element (i,j) of the first matrix ($M_i$) quantifies each corresponding feature-pair ($F_iF_j$) based on their co-occurrence in the analyzed signatures in run $r_i$; and forming 420b a second matrix (T), wherein each element ($T_{(i,j)}$) of the second matrix (T) is assigned the sum of the corresponding row ($F_i$) of the corresponding first matrix ($M_i$).

The computer program 40 comprises a third code segment 430 for forming a vector (C, e.g. C=$C_{F1}$, $C_{F2}$, ... $C_{Fn}$) of size (F) wherein each element ($C_{Fi}$) of said vector is assigned the average of the corresponding row ($T_i$) for all columns (1 to N) of the second matrix (T).

The computer program 40 comprises a fourth code segment 440 for sorting each value of vector (C) in descending order, resulting in ranking each feature ($F_i$) represented by each element of the vector (C) in descending order. The computer program 40 comprises a fifth code segment 450 for forming a novel set of signatures based on the ranked features by combining at least two features of signatures with similar ranking.

In an embodiment the computer program product comprises a computer program 40 for processing by a computer comprising code segments arranged, when run by a device having computer-processing properties, for performing all of the method steps defined in the method 10.

In an embodiment, the method 10 or device 30 provides information, such as groups of multiple molecular signatures of biological data, which may assist a physician in reaching a diagnosis or treating a patient.

Thus in an embodiment, use of the method 10 or the device 30 for statistically analyzing clinical data is provided.

For example, within a dataset which contains a total of 100 patients, some of the patients have a particular outcome, such as recurrence of cancer, while some have a different outcome. Multiple signatures are discovered and characterized as provided above. For example, signatures are evaluated based on the ability to predict recurrence status for each patient. A diagnostic assay measures all the relevant features from the original study. Given a new patient, the clinician may generate multiple signatures that each predict recurrence for the given patient and evaluate each of them based on some property of the signature. For example, the clinician may use only signatures that contain information about genes associated with a biological pathway related to a specific therapy.

In an embodiment, use of the method 10 or the device 30 for designing assays based on multiple molecular signatures is provided.

Based on the above, assays may be designed that contain a smaller subset of features generated. In this case the features are selected based on some property, for example, genes known to be related to the disease or for example, features (genes) with better properties for the measurement device.

In an embodiment, use of the method 10 or the device 30 for interpreting assays based on multiple molecular signatures is provided.

Given an assay according to above, a clinician may use the characterization to design a second assay to interpret the output from the first assay. Based on existence or non-existence of signal for some of the features on the assay readout, the clinician may infer additional information for features that are not explicitly measured with the first assay. For example, knowing that features A and B largely co-occur in the molecular signatures and because the first assay provides a measurement of just feature A, the clinician may then choose to infer the likely measurement of feature B and thus obtain additional clinically relevant information about the patient.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A non-transitory computer readable storage medium with an executable program stored thereon, wherein the program instructs a processor to perform operations, comprising:

generating a set of multiple signatures of biological data comprising a number of features ($F=\{F_1, F_2, \ldots, F_n\}$) by running a feature subset selection algorithm on the biological data N times, and for each run ($r_i$) of a number of runs ($\{r_1, r_2, \ldots, r_N\}$), wherein the biological data is generated based on biological samples gathered from a plurality of patients;

forming a first matrix ($M_i$) of size (F×F), wherein each matrix element (i,j) of the first matrix ($M_i$) quantifies each corresponding feature-pair ($F_iF_j$) based on their co-occurrence in the analyzed signatures in run $r_i$; and forming a second matrix (T) of size (F×N), wherein each element ($T_{(i,j)}$) of the second matrix (T) is assigned the sum of the corresponding row ($F_i$) of the corresponding first matrix ($M_i$);

forming a vector (C) of size (F) wherein each element ($C_{Fi}$) of the vector is assigned the average of the corresponding row ($T_i$) for all columns (1 to N) of the second matrix (T);

sorting each value of vector (C) in descending order, resulting in ranking each feature ($F_i$) represented by each element of the vector (C) in descending order;

computing a novel set of signatures based on the ranked features by combining at least two features of signatures with similar ranking; and implementing the novel set of signatures in a diagnostic assay to predict recurrence status for a given patient wherein each signature is evaluated based on a known property.

2. The non-transitory computer readable storage medium according to claim 1, wherein the signatures are molecular signatures.

3. The non-transitory computer readable storage medium according to claim 2, wherein the molecular signatures are chosen from the group comprising: nucleotide sequence, genetic variation, methylation status or genetic expression.

4. The non-transitory computer readable storage medium according to claim 1, wherein the feature subset selection is pattern discovery.

5. A device for generating data indicative of novel signatures of biological data, comprising:

a non-transitory computer readable storage medium storing a set of instructions; and a processor that executes the instructions, wherein the instructions cause the processor to:

generate a set of multiple signatures of biological data by running a feature subset selection algorithm on the biological data N times, wherein the biological data is generated based on biological samples gathered from a plurality of patients;

for each run ($r_1$), of a number of runs ($\{r_1, r_2, \ldots, r_N\}$), form a first matrix ($M_i$) of size (F×F), wherein each matrix element (i,j) of the first matrix ($M_i$) quantifies each corresponding feature-pair ($F_iF_j$) based on their co-occurrence in the analyzed signatures in run $r_i$; and form a second matrix (T) of size (F×N), wherein each element ($T_{(i,j)}$) of the second matrix (T) is assigned the sum of the corresponding row ($F_i$) of the corresponding first matrix ($M_i$);

form a vector (C) of size (F) wherein each element ($C_{Fi}$) of the vector is assigned the average of the corresponding row ($T_i$) for all columns (1 to N) of the second matrix (T);

sort each value of vector (C) in descending order, resulting in ranking each feature ($F_i$) represented by each element of the vector (C) in descending order;

compute a novel set of signatures based on the ranked features by combining at least two features of signatures with similar ranking; and implement the novel set of signatures in a diagnostic assay to predict recurrence status for a given patient wherein each signature is evaluated based on a known property.

6. The non-transitory computer readable storage medium according to claim 1, wherein the biological samples are gathered using one of a Computer Tomography (CT) system, a Magnetic Resonance Imaging (MM) system, an Ultrasound Imaging (US) system, or a combination thereof.

7. A method, comprising:

receiving patient data associated with a current patient, the patient data generated based on a biological sample gathered from the current patient;

generating a set of multiple signatures of biological data comprising a number of features ($F=\{F_1, F_2, \ldots, F_n\}$) by running a feature subset selection algorithm on the biological data N times, and for each run ($r_i$) of a number of runs ($\{r_1, r_2, \ldots, r_N\}$);

forming a first matrix ($M_i$) of size (F×F), wherein each matrix element (i,j) of the first matrix ($M_i$) quantifies each corresponding feature-pair ($F_iF_j$) based on their co-occurrence in the analyzed signatures in run $r_i$; and forming a second matrix (T) of size (F×N), wherein each element ($T_{(i,j)}$) of the second matrix (T) is assigned the sum of the corresponding row ($F_i$) of the corresponding first matrix (MO;

forming a vector (C) of size (F) wherein each element ($C_{Fi}$) of the vector is assigned the average of the corresponding row ($T_i$) for all columns (1 to N) of the second matrix (T);

sorting each value of vector (C) in descending order, resulting in ranking each feature ($F_i$) represented by each element of the vector (C) in descending order;

computing a novel set of signatures based on the ranked features by combining at least two features of signatures with similar ranking;

implementing the novel set of signatures in a diagnostic assay to predict recurrence status for a given patient wherein each signature is evaluated based on a known property; and determining a clinical state of the patient based on the patient data, the diagnostic assay and the novel set of signatures.

\* \* \* \* \*